United States Patent [19]
Albus et al.

[11] Patent Number: 6,153,651
[45] Date of Patent: Nov. 28, 2000

[54] ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

[75] Inventors: Udo Albus, Florstadt; Joachim Brendel, Bad Vilbel; Heinz-Werner Kleemann, Bischofsheim; Hans Jochen Lang, Hofheim; Wolfgang Scholz, Eschborn; Jan-Robert Schwark, Frankfurt; Andreas Weichert, Egelsbach, all of Germany

[73] Assignee: Hoechst Aktiengesellschaft, Frankfurt am Main, Germany

[21] Appl. No.: 08/808,295

[22] Filed: Feb. 28, 1997

[30] Foreign Application Priority Data

Mar. 4, 1996 [DE] Germany .......................... 196 08 162

[51] Int. Cl.⁷ ........................ A61K 31/165; C07C 233/64
[52] U.S. Cl. .......................... 514/617; 514/520; 514/521; 514/522; 514/621; 514/622; 514/307; 514/311; 514/357; 558/415; 564/142; 564/162; 564/163; 564/169; 564/176; 564/177; 546/139; 546/152; 546/329
[58] Field of Search ..................................... 514/621, 520, 514/521, 522, 622, 307, 311, 357; 558/415; 564/162, 163, 169, 142, 176, 177; 546/152, 139, 329

[56] References Cited

U.S. PATENT DOCUMENTS

| | | |
|---|---|---|
| 5,292,755 | 3/1994 | Englert et al. .......................... 514/331 |
| 5,461,066 | 10/1995 | Gericke et al. . |
| 5,670,544 | 9/1997 | Weichert et al. ....................... 514/618 |
| 5,679,712 | 10/1997 | Schwark et al. ........................ 514/621 |
| 5,719,169 | 2/1998 | Kleenman et al. . |
| 5,753,680 | 5/1998 | Gericke et al. . |

FOREIGN PATENT DOCUMENTS

| | | |
|---|---|---|
| 627 413 | 12/1994 | European Pat. Off. . |
| 667 341 | 8/1995 | European Pat. Off. . |
| 699 666 | 3/1996 | European Pat. Off. . |
| 0640588 | 1/1995 | Germany . |
| 43 25 822 | 2/1995 | Germany . |
| 4421495 | 12/1995 | Germany . |
| WO 9426709 | 11/1994 | WIPO . |

*Primary Examiner*—Shailendra Kumar
*Attorney, Agent, or Firm*—Finnegan, Henderson, Farabow, Garrett and Dunner, L.L.P.

[57] ABSTRACT

Ortho-substituted benzoylguanidines, process for their preparation, their use as a medicament or diagnostic, and medicament comprising them.

Ortho-substituted benzoylguanidines of the formula I

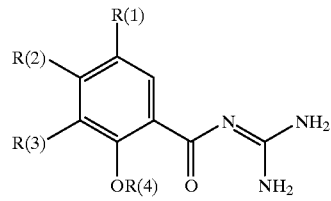

in which R(1) to R(4) have the meanings given in the claims, are suitable, as antiarrhythmic pharmaceuticals having a cardioprotective component, for the prophylaxis and treatment of infarction and for the treatment of angina pectoris. They also inhibit, in a preventive manner, the pathophysiological processes associated with the genesis of ischemically induced damage, in particular associated with the triggering of ischemically induced cardiac arrhythmias.

23 Claims, No Drawings

ORTHO-SUBSTITUTED BENZOYLGUANIDINES, PROCESS FOR THEIR PREPARATION, THEIR USE AS A MEDICAMENT OR DIAGNOSTIC, AND MEDICAMENT COMPRISING THEM

The invention relates to benzoylguanidines of the formula I

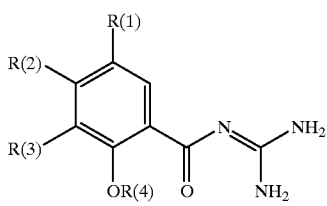

in which:
R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, S or NR(5),
a is zero or 1;
b is zero, 1 or 2;
c is zero, 1, 2 or 3;
R(5) is H, alkyl having 1, 2, 3 or 4 carbon atoms or —$C_dH_{2d}R(6)$;
d is zero, 1, 2, 3 or 4;
R(6) is cycloalkyl having 3, 4, 5, 6, 7 or 8 carbon atoms, phenyl, biphenylyl or naphthyl,
where the aromatic radicals phenyl, biphenylyl or naphthyl are unsubstituted or substituted by 1–3 substituents selected from the group consisting of F, Cl, $CF_3$, methyl, methoxy and NR(7)R(8); R(7) and R(8) are,
independently, H or alkyl having 1, 2, 3 or 4 carbon atoms; or
R(1) is —SR(10), —OR(10) or —CR(10)R(11)R(12);
R(10) is —$C_fH_{2f}$-cycloalkyl having 3, 4, 5, 6, 7 or 8 carbon atoms in the cycloalkyl ring, or phenyl,
where phenyl is unsubstituted or substituted by 1–3 substituents selected from the group consisting of F, Cl, $CF_3$, $CH_3$, methoxy, hydroxyl, amino, methylamino and dimethylamino;
f is zero, 1 or 2;
R(11) and R(12) are,
independently of each other, defined as R(10) or are hydrogen or alkyl having 1, 2, 3 or 4 carbon atoms;
or
R(1) is phenyl, naphthyl, biphenylyl or heteroaryl having 1, 2, 3, 4, 5, 6, 7, 8 or 9 carbon atoms, with the latter being linked via a C atom or an N atom of the ring,
which are in each case unsubstituted or substituted by 1–3 substituents selected from the group consisting of F, Cl, $CF_3$, $CH_3$, methoxy, hydroxyl, amino, methylamino and dimethylamino,
or
R(1) is —SR(13), —OR(13), —NHR(13), —NR(13)R(14), —CHR(13)R(15), —C[R(15)R(16)OH], —C≡CR(18), —C[R(19)]=CHR(18), —$C[R(20)R(21)]_k$13 (CO)—$[CR(22)R(23)]_l$—R(24),
k is zero, 1, 2, 3 or 4;
l is zero, 1, 2, 3 or 4;
R(13) and R(14) are,
identically or differently, —$(CH_2)_g$—$(CHOH)_h$—$(CH_2)_i$—$(CHOH)_j$—R(17) or —$(CH_2)_g$—O—$(CH_2$—$CH_2O)_h$—R(24);
R(17) is hydrogen or methyl,
g, h and i are,
identically or differently, zero, 1, 2, 3 or 4;
j is 1, 2, 3 or 4;
R(15) and R(16) are,
identically or differently, hydrogen, alkyl having 1, 2, 3, 4, 5 or 6 carbon atoms, or are, together with the carbon atom carrying them, cycloalkyl having 3, 4, 5, 6, 7 or 8 carbon atoms;
R(18) is
phenyl,
which is unsubstituted or substituted by 1–3 substituents selected from the group consisting of F, Cl, $CF_3$, methyl, methoxy and NR(25)R(26);
R(25) and R(26) are
H or alkyl having 1, 2, 3 or 4 carbon atoms;
or
R(18) is heteroaryl having 1, 2, 3, 4, 5, 6, 7, 8 or 9 carbon atoms which is unsubstituted or substituted as phenyl;
or
R(18) is alkyl having 1, 2, 3, 4, 5 or 6 carbon atoms which is unsubstituted or substituted by 1–3 OH;
or
R(18) is
cycloalkyl having 3, 4, 5, 6, 7 or 8 carbon atoms;
R(19), R(20), R(21), R(22) and R(23) are,
identically or differently, hydrogen or methyl;
R(24) is H, alkyl having 1, 2, 3, 4, 5 or 6 carbon atoms, cycloalkyl having 3, 4, 5, 6, 7 or 8 carbon atoms or —$C_mH_2m$—R(18);
m is 1, 2, 3 or 4;
R(2) and R(3) are
defined as R(1);
R(4) is alkyl having 1, 2, 3 or 4 carbon atoms;
and the pharmaceutically tolerated salts thereof.
Compounds of the formula I are preferred in which:
R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen;
a is zero or 1;
b is zero, 1 or 2;
c is zero, 1, 2 or 3;
or
R(1) is —SR(10) or —OR(10);
R(10) is —$C_fH_{2f}$-cycloalkyl having 3, 4, 5, 6, 7 or 8 carbon atoms in the cycloalkyl ring, or phenyl
where phenyl is unsubstituted or substituted by 1–3 substituents selected from the group consisting of F, Cl, $CF_3$, $CH_3$, methoxy, hydroxyl, amino, methylamino and dimethylamino;
f is zero or 1;
or
R(1) is phenyl, naphthyl, biphenylyl or heteroaryl having 1, 2, 3, 4, 5, 6, 7, 8 or 9 carbon atoms, with the latter being linked via a C atom or N atom of the ring,
which are unsubstituted or substituted by 1–3 substituents selected from the group consisting of F, Cl, $CF_3$, $CH_3$, methoxy, hydroxyl, amino, methylamino and dimethylamino, or R(1) is —SR(13), —OR(13), —NHR(13), —NR(13)R(14), —C≡CR(18) or —C[R(19)]═CHR(18);

R(13) and R(14) are,
identically or differently, —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);

R(17) is hydrogen or methyl, g, h and i are,
identically or differently, zero, 1 or 2;

j is 1 or 2;

R(18) is
phenyl,
which is unsubstituted or substituted by 1–3 substituents selected from the group consisting of F, Cl, CF$_3$, methyl, methoxy and NR(25)R(26);

R(25) and R(26) are
H or alkyl having 1, 2, 3 or 4 carbon atoms;

or

R(18) is heteroaryl having 1, 2, 3, 4, 5, 6, 7, 8 or 9 carbon atoms, which is unsubstituted or substituted as phenyl;

or

R(18) is alkyl having 1, 2, 3, 4, 5 or 6 carbon atoms, which is unsubstituted or substituted by 1–3 OH;

or

R(18) is
cycloalkyl having 3, 4, 5, 6, 7 or 8 carbon atoms;

R(19) is hydrogen or methyl;

R(2) and R(3) are
defined as R(1);

R(4) is alkyl having 1 or 2 carbon atoms;

and the pharmaceutically tolerated salts thereof.

Compounds of the formula I are very particularly preferred in which:

R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or X$_a$—(CF$_2$)$_c$—CF$_3$;

X is oxygen;

a is zero or 1;

c is zero or 1;

or

R(1) is —SR(10) or —OR(10);

R(10) is cycloalkyl having 4, 5 or 6 carbon atoms, or phenyl,
where phenyl is unsubstituted or substituted by 1–3 substituents selected from the group consisting of F, Cl, CF$_3$, CH$_3$, methoxy, hydroxyl, amino, methylamino and dimethylamino;

or

R(1) is quinolyl, isoquinolyl or pyridyl,
which are linked via a C atom or N atom of the ring; and which are unsubstituted or substituted by 1–3 substituents selected from the group consisting of F, Cl, CF$_3$, CH$_3$, methoxy, hydroxyl, amino, methylamino and dimethylamino, or R(1) is phenyl,
which is unsubstituted or substituted by 1–3 substituents selected from the group consisting of F, Cl, CF$_3$, CH$_3$, methoxy, hydroxyl, amino, methylamino and dimethylamino, or R(1) is —C≡CR(18);

R(18) is
phenyl or cycloalkyl having five or 6 carbon atoms;

R(2) and R(3) are
defined as R(1);

R(4) is methyl;

and the pharmaceutically tolerated salts thereof.

Compounds of the formula I are especially preferred in which

R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or X$_a$—CF$_3$;

X is oxygen;

a is zero or 1;

R(2) and R(3) are
defined as R(1);

R(4) is methyl;

and the pharmaceutically tolerated salts thereof.

Heteroaryl having 1, 2, 3, 4, 5, 6, 7, 8 or 9 carbon atoms is understood to mean radicals which are derived from phenyl or naphthyl, in which one or more CH groups is/are replaced by N and/or in which at least two adjacent CH groups are replaced by S, NH or O (with the formation of a five-membered aromatic ring). In addition, one or both atoms of the fusion site of bicyclic radicals can be N atoms (as in indolizinyl). Furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl; in particular furanyl, thienyl, pyrrolyl, imidazolyl, pyrazolyl, triazolyl, thiazolyl, pyridyl, indolyl, quinolyl and isoquinolyl, are regarded, in particular, as being heteroaryl having 1, 2, 3, 4, 5, 6, 7, 8 or 9 carbon atoms.

If one of the substituents R(1) to R(4) contains one or more centers of asymmetry, these centers can be either in the S or the R configuration. The compounds can be present as optical isomers, as diastereomers, as racemates or as mixtures of these.

The designated alkyl radicals can be straight-chain or branched.

The invention furthermore relates to a process for preparing compound I, which comprises reacting a compound of the formula II $$\begin{array}{c}\text{R(2)}\\\text{R(3)}\end{array}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\end{array}$$

in which R(1) to R(4) have the given meaning and L is a leaving group which can readily be substituted nucleophilically, with guanidine.

The activated acid derivatives of the formula II, in which L is an alkoxy group, preferably a methoxy group, a phenoxy group, a phenylthio group, a methylthio group or a 2-pyridylthio group, or a nitrogen heterocycle, preferably 1-imidazolyl, are advantageously obtained, in a manner known per se, from the underlying carbonyl chlorides (formula II, L═Cl), which, for their part, can in turn be prepared, in a manner known per se, from the underlying carboxylic acids (formula II, L=OH), for example using thionyl chloride.

In addition to the carbonyl chlorides of the formula II (L=Cl), other activated acid derivatives of the formula II can also be prepared, in a manner known per se, from the underlying benzoic acid derivatives (formula II, L=OH), such as methyl esters of the formula II in which L=OCH$_3$ by treating with gaseous HCl in methanol, the imidazolides of the formula II by treating with carbonyldiimidazole [L=1-imidazolyl, Staab, Angew. Chem. Int. Ed. Engl. 1, 351–367 (1962)], the mixed anhydrides II using Cl—COOC$_2$H$_5$ or tosyl chloride in the presence of triethylamine in an inert solvent, in addition to which there is also the activation of benzoic acids with dicyclohexylcarbodiimide (DCC) or with O-[(cyano(ethoxycarbonyl)-methylene)amino]-1,1,3,3-tetramethyluronium tetrafluoroborate ("TOTU")[Weiss and Krommer, Chemiker Zeitung 98, 817 (1974)]. A series of suitable methods for preparing activated carboxylic acid derivatives of the formula II are given, with citation of the source literature, on p. 350 of J. March, Advanced Organic Chemistry, Third Edition (John Wiley & Sons, 1985).

The reaction of an activated carboxylic acid derivative of the formula II with guanidine is effected in a manner known per se in a protic or aprotic, polar but inert organic solvent. In this context, methanol, isopropanol or THF, at a temperature of from 20° C. up to the boiling temperature of the solvents, have proved to be advantageous when reacting the methyl benzoates (II, L=OMe) with guanidine. Most reactions of compounds 11 with salt-free guanidine were advantageously carried out in aprotic, inert solvents such as THF, dimethoxymethane or dioxane. However, if a base such as NaOH is employed, water can also be used as solvent when reacting 11 with guanidine.

If L=Cl, the reaction is advantageously carried out in the presence of an added acid-capturing agent, for example in the form of excess guanidine, for the purpose of removing the hydrohalic acid.

Some of the underlying benzoic acid derivatives of the formula II are known and described in the literature. The unknown compounds of the formula II may be prepared using methods which are known from the literature. The resulting benzoic acids are converted into novel I compounds using one of the above-described process variants.

Introduction of some substituents in the 3, 4 and 5 positions is achieved using the methods, which are known from the literature, of palladium-mediated cross-coupling of aryl halides or aryl triflates with, for example, organostannanes, organoboronic acids or organoboranes or organocopper or organozinc compounds.

In general, benzoylguanidines I are weak bases and can bind acid with the formation of salts. Suitable acid addition salts are salts of all the pharmacologically tolerated acids, for example halides, in particular hydrochlorides, lactates, sulfates, citrates, tartrates, acetates, phosphates, methylsulfonates and p-toluenesulfonates.

The I compounds are substituted acylguanidines.

Compounds which are similar to the I compounds are known from European Laid-Open Specification 640 588 A 1 (HOE 93/F 254). However, the known compounds do not contain any alkoxy radical in the 2 position, which radical distinguishes the novel compounds from the known compounds.

In addition, similar compounds are likewise known from German Laid-Open Specification 44 21 495, which compounds, however, always contain a heteroaryloxy substituent; by contrast, the novel compounds do not possess this heteroaryloxy substituent.

As compared with the known compounds, the novel compounds are notable for exhibiting an extraordinarily high activity in inhibiting Na$^+$/H$^+$ exchange.

Like the known compounds, they do not possess any undesirable and disadvantageous salidiuretic properties but nevertheless possess very good antiarrhythmic properties such as are important, for example, for treating diseases which occur in association with symptoms of oxygen deficiency. As a consequence of their pharmacological properties, the compounds, as antiarrhythmic pharmaceuticals having a cardioprotective component, are outstandingly suitable for the prophylaxis and treatment of infarction and for treating angina pectoris, while they also inhibit, or strongly diminish, in a preventive manner, the pathophysiological processes associated with the genesis of ischemically induced damage, in particular in association with the triggering of ischemically induced cardiac arrhythmias. On account of their protective effects against pathological hypoxic and ischemic situations, the novel compounds of the formula I can, as a consequence of inhibition of the cellular Na+/H+ exchange mechanism, be used as pharmaceuticals for treating all acute or chronic damage which is provoked by ischemia, or diseases which are primarily or secondarily induced thereby. This relates to their use as pharmaceuticals for surgical interventions, for example in association with organ transplantations, with it being possible to use the compounds for protecting the organs in the donor before and during the removal, for protecting removed organs, for example when treating them with, or storing them in, physiological bathing fluids, and also when transferring them into the recipient. The compounds are likewise valuable pharmaceuticals, having a protective action, for use when carrying out angioplastic surgical interventions, for example on the heart and on peripheral blood vessels. In conformity with their protective effect against ischemically induced damage, the compounds are also suitable for use as pharmaceuticals for treating ischemias of the nervous system, in particular the CNS, in association with which they are suitable, for example, for treating stroke and cerebral edema. In addition to this, the novel compounds of the formula I are likewise suitable for treating forms of shock, for example allergic, cardiogenic, hypovolemic and bacterial shock.

Over and above this, the novel compounds of the formula I are notable for the powerful inhibitory effect which they exert on the proliferation of cells, for example fibroblast cell proliferation and proliferation of the smooth muscle cells of the blood vessels. For this reason the compounds of formula I are suitable, as valuable therapeutic agents, for use in diseases in which cell proliferation constitutes a primary or secondary cause, and can, therefore, be used as antiatherosclerotics, and as agents against late complications in diabetes, cancerous diseases, fibrotic diseases, such as pulmonary fibrosis, hepatic fibrosis or renal fibrosis, and organ hypertrophies and hyperplasias, in particular in hyperplasia or hypertrophy of the prostate.

The novel compounds are effective inhibitors of the cellular sodium/proton antiporter (Na$^+$/H$^+$ exchanger), which, in a large number of diseases (essential hypertension, atherosclerosis, diabetes, etc.), is also elevated in cells, for example erythrocytes, thrombocytes or leukocytes, which are readily accessible to measurement. The novel compounds are therefore suitable for use as simple and outstandingly good scientific tools, for example in their employment as diagnostic agents for identifying and differentiating particular forms of hypertension and also atherosclerosis, diabetes, proliferative diseases, etc. In addition to this, the compounds of the formula I are suitable for preventive therapy, for preventing the genesis of high blood pressure, for example the genesis of essential hypertension.

In this context, pharmaceuticals which comprise a I compound can be administered orally, parenterally, intravenously, rectally or by inhalation, with the preferred form of administration depending on the particular features of the disease. In this context, the I compounds can be used either alone or together with pharmaceutical auxiliary substances, both in veterinary medicine and in human medicine.

Based on his specialist knowledge, the skilled person is familiar with the auxiliary substances which are suitable for the desired pharmaceutical formulation. For example, antioxidants, dispersants, emulsifiers, defoamers, taste corrigents, preservatives, solubilizers or dyes can be used in addition to solvents, gelatinizing agents, suppository bases, tablet auxiliary substances and other active compound excipients.

For an oral use form, the active compounds are mixed with the additives, such as carrier substances, stabilizers or inert diluents, which are suitable for the purpose and brought, using the customary methods, into the administration forms, such as tablets, coated tablets, hard gelatin capsules or aqueous, alcoholic or oily solutions, which are suitable. Gum arabic, magnesium hydroxide, magnesium carbonate, potassium phosphate, lactose, glucose or starch, in particular corn starch, can, for example, be used as inert excipients. In this context, the preparation can be effected either as a dry granulate or as a wet granulate. Examples of suitable oily carrier substances or solvents are vegetable or animal oils, such as sunflower oil or cod liver oil.

For subcutaneous or intravenous administration, the active compounds, if desired together with the substances which are customarily suitable for the purpose, such as solubilizers, emulsifiers or other auxiliary substances, are brought into solution, suspension or emulsion. Examples of suitable solvents are: water, physiological sodium chloride solution or alcohols, for example ethanol, propanol or glycerol, and, in addition, also sugar solutions, such as glucose or mannitol solutions, or else a mixture composed of the different solvents mentioned.

Solutions, suspensions or emulsions of the active compound of the formula I in a pharmaceutically harmless solvent, such as, in particular, ethanol or water, or a mixture of the solvents, are suitable, for example, for use as a pharmaceutical formulation for administration in the form of aerosols or sprays.

If required, the formulation can also comprise other pharmaceutical auxiliary substances, such as surfactants, emulsifiers and stabilizers, and also a propellant gas. Such a preparation customarily comprises the active compound in a concentration of from about 0.1 to 10, in particular of from about 0.3 to 3, % by weight.

The dose of the active compound of the formula I to be administered, and the frequency of administration, depend on the strength and duration of the effect of the compounds used; they also depend on the nature and severity of the disease to be treated and on the sex, age, weight and individual responsiveness of the mammalian subject to be treated.

On average, the daily dose of a compound of the formula I is, in the case of a patient of approximately 75 kg in weight, at least 0.001 mg/kg, preferably 0.01 mg/kg up to at most 10 mg/kg, preferably 1 mg/kg, of body weight. In the case of acute attacks of the disease, for example immediately after suffering a cardiac infarction, higher and, in particular, more frequent doses may also be necessary, for example up to 4 individual doses per day. Up to 200 mg per day can be necessary in the case of i.v. use, in particular, for example in the case of an infarction patient in intensive care.

List of abbreviations:

| | |
|---|---|
| MeOH | methanol |
| DMF | N,N-dimethylformamide |
| RT | room temperature |
| EA | ethyl acetate (EtOAc) |
| m.p. | melting point |
| THF | tetrahydrofuran |
| eq. | equivalent |

Experimental part

General protocol for preparing benzoylguanidines (I)

Variant A: from benzoic acids (II, L=OH)

1.0 eq. of the benzoic acid derivative of the formula II is dissolved or suspended in anhydrous THF (5 ml/mmol) and 1.1 eq. of carbonyldiimidazole are then added. After stirring at RT for 2 hours, 5.0 eq. of guanidine are introduced into the reaction solution. After this mixture has been stirred overnight, the THF is distilled off under reduced pressure (rotary evaporator), water is added, the pH is adjusted to from 6 to 7 with 2 N HCl and the corresponding benzoylguanidine (formula I) is filtered off. The benzoylguanidines which are obtained in this way can be converted into the corresponding salts by treating them with aqueous, methanolic or ethereal hydrochloric acid or other pharmacologically tolerated acids.

General protocol for preparing benzoyl guanidines (I)

Variant B: from alkyl benzoates (II, L=O-alkyl)

1.0 eq. of the alkylbenzoate of the formula II and 5.0 eq. of guanidine (free base) are dissolved in isopropanol or suspended in THF and heated to boiling until reaction is complete (monitoring by thin layer chromatography) (typical reaction time, from 2 to 5 h). The solvent is distilled off under reduced pressure (rotary evaporator), and the residue is taken up in EA and this solution is washed 3× with a solution of $NaHCO_3$. It is then dried over $Na_2SO_4$ and the solvent is distilled off in vacuo; the residue is chromatographed on silica gel using a suitable eluent, for example EA/MeOH 5:1.

(Salt formation, cf. variant A)

EXAMPLE 1

2,3-Dimethoxy-5-trifluoromethylbenzoylguanidine hydrochloride:

Colorless crystals, m.p. 166° C. (decomposition)

Synthesis route:

a) Methyl 2-chloro-3-iodo-5-trifluoromethylbenzoate from methyl 2-chloro-5-trifluoromethylbenzoate by reaction, at RT for 24 h, with 1 equivalent of N-iodosuccinimide in 5 equivalents of trifluoromethanesulfonic acid, colorless oil, $(M+H)^+$: 364 b) 2,3-Dimethoxy-5-trifluoromethylbenzoic acid from methyl 2-chloro-3-iodo-5-trifluoromethylbenzoate (1 a) by reaction, under reflux and within the space of 1 h, with 10 equivalents of 30% sodium methoxide solution in the presence of 0.25 of an equivalent of copper(II) chloride in abs. DMF. Aqueous working-up and extraction with EA yields a brownish oil, $(M+H)^+$: 251 c) 2,3-Dimethoxy-5-trifluoromethylbenzoylguanidine hydrochloride from 1 b) in accordance with process A, colorless crystals m.p. 166° C. (decomposition).

EXAMPLE 2

2-Methoxy-3-iodo-5-trifluoromethylbenzoylguanidine hydrochloride:

Colorless crystals, m.p. 150° C. (decomposition)

Synthesis route:

a) 2-Methoxy-3-iodo-5-trifluoromethylbenzoic acid from 1 a) by reaction, at RT and within the space of 2 h, with 1.1 equivalents of 30% sodium methoxide solution in the presence of 0.3 of an equivalent of copper(II) chloride in abs. DMF. Aqueous working-up and extraction with EA yields colorless crystals, m. p. 120–25° C.

b) 2-Methoxy-3-iodo-5-trifluoromethylbenzoylguanidine hydrochloride from 2 a) in accordance with process A, colorless crystals, m.p. 150° C. (decomposition)

EXAMPLE 3

2-Methoxy-3-cyclopentyl-5-trifluoromethylbenzoylguanidine hydrochloride:

Colorless crystals, m.p. 210° C. (decomposition)

Synthesis route:

a) Methyl 2-chloro-3-cyclopentyl-5-trifluoromethylbenzoate from 1 a) by means of cross-coupling with 1.5 equivalents of cyclopentylzinc chloride (from cyclopentylmagnesium chloride by transmetallation with zinc(II) chloride etherate in THF) by stirring, at RT, in the presence of catal. palladium(II) [1,1'-bis-(diphenylphosphino)ferrocene] chloride and copper(I) iodide, aqueous working-up, extraction with ethyl acetate and subsequent column chromatography on silica gel using ethyl acetate/n-heptane (3:7), colorless oil, $(M+H)^+$: 306 b) 2-Methoxy-3-cyclopentyl-5-trifluoromethylbenzoic acid by reaction, at reflux and within the space of 1 h, with 10 equivalents of 30% sodium methoxide solution in the presence of 0.25 of an equivalent of copper(II) chloride in abs. DMF. Aqueous working-up and extraction with EA yields a colorless oil, $(M+H)^+$: 289 c) 2-Methoxy-3-cyclopentyl-5-trifluoromethylbenzoylguanidine hydrochloride from 3 b) in accordance with process A, colorless crystals, m.p. 210° C. (decomposition)

EXAMPLE 4

2-Methoxy-5-trifluoromethylbenzoylguanidine hydrochloride:

Colorless crystals, m.p. 208° C. (decomposition)

Synthesis route:

a) 2-Methoxy-5-trifluoromethylbenzoic acid from methyl 2-chloro-5-trifluoromethylbenzoate by reaction, at 100° C. and within the space of 1.5 h, with 10 equivalents of 30% sodium methoxide solution in the presence of 0.25 of an equivalent of copper(II) chloride in abs. DMF. Aqueous working-up and column chromatography yields colorless crystals, m.p. 108–10° C.

b) 2-Methoxy-5-trifluoromethylbenzoylguanidine hydrochloride from 4 a) in accordance with process A, colorless crystals, m.p. 208° C. (decomposition)

EXAMPLE 5

2-Methoxy-4-methylbenzoylguanidine hydrochloride: Colorless crystals, m.p. 213° C.

Synthesis route:

a) 2-Methoxy-4-methylbenzoic acid from methyl 2-chloro-4-methylbenzoate in analogy with 3 b), colorless solid, m.p. 212° C.

b) 2-Methoxy-4-methylbenzoylguanidine hydrochloride from 5 a) in accordance with the general protocol.

EXAMPLE 6

3,5-Bis-tert-butyl-2-methoxybenzoylguanidine hydrochloride:

Colorless crystals, m.p. 114° C.

Synthesis route:

a) Methyl 3,5-bis-tert-butyl-2-methoxybenzoate from methyl 3,5-bis-tert-butylsalicylate using methyl iodide in the presence of potassium carbonate in DMF, colorless oil, $(M+H)^+$=278.

b) 3,5-Bis-tert-butyl-2-methoxybenzoylguanidine hydrochloride from 6 a) in accordance with the general protocol.

EXAMPLE 7

2,4-Dimethoxy-5-trifluoromethylbenzoylguanidine hydrochloride:

Colorless crystals, m.p. 207° C.

Synthesis route:

a) Methyl 2,4-dimethoxy-5-bromobenzoate from 5-bromo-2,4-hydroxybenzoic acid using methyl iodide in DMF in the presence of potassium carbonate, colorless crystals, m.p. 115° C.

b) Methyl 2,4-dimethoxy-5-trifluoromethylbenzoate from 7 a) by heating at 90° C. together with potassium trifluoroacetate in NMP in the presence of copper(I) iodide, colorless crystals, m.p. 125° C.

c) 2,4-Dimethoxy-5-trifluoromethylbenzoylguanidine hydrochloride: from 7 a) in accordance with the general protocol.

Pharmacological data:

Inhibition of the rabbit erythrocyte $Na^+/H^+$ exchanger New Zealand White rabbits (Ivanovas) were given a standard diet containing 2% cholesterol for six weeks in order to activate $Na^+/H^+$ exchange and thus render it possible to use flame photometry to determine the influx of Na+into the erythrocytes by way of $Na^+/H^+$ exchange. The blood was withdrawn from the aural arteries and rendered incoagulable by adding 25 IU of potassium heparin. A part of each sample was used for determining the hematocrit in duplicate by means of centrifugation. Aliquots of in each case 100 $\mu l$ were used to measure the initial content of $Na^+$ in the erythrocytes.

In order to determine the amiloride-sensitive sodium influx, 100 $\mu l$ of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl) aminomethane). After that, the erythrocytes were washed three times with an ice cold solution of $MgCl_2$/ouabain (mmol/l: 112 $MgCl_2$, 0.1 ouabain) and hemolyzed in 2.0 ml of distilled water. The intracellular content of sodium was determined by flame photometry.

The net influx of Na⁺ was calculated from the difference between the initial sodium values and the sodium content of the erythrocytes after incubation. The amiloride-inhibitable sodium influx was obtained from the difference in the sodium content of the erythrocytes after incubation with and without $3\times10^{-4}$ mol/l amiloride. The same procedure was used in the case of the novel compounds.

Results

Inhibition of the Na⁺/H⁺ exchanger:

| Example | IC$_{50}$(mol/l) |
|---|---|
| 1 | $0.053 \times 10^{-6}$ |
| 2 | $0.017 \times 10^{-6}$ |
| 5 | $>10^{-6}$ |
| 6 | $1 \times 10^{-6}$ |
| 7 | $0.2 \times 10^{-6}$ |

What is claimed is:

1. An ortho-substituted benzoylguanidine of the formula I

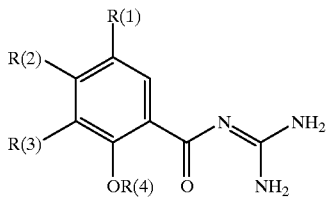

in which:

R(1) is H, F, Cl, Br, I, CN, NO₂, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S or NR(5),
a is zero or 1;
b is zero, 1 or 2;
c is zero, 1, 2 or 3;
R (5) is H, alkyl having 1, 2, 3 or 4 carbon atoms or —C$_d$H$_{2d}$R(6);
d is zero, 1, 2, 3 or 4;
R(6) is cycloalkyl having 3, 4, 5, 6, 7 or 8 carbon atoms, phenyl, biphenylyl or naphthyl,
where the aromatic radicals phenyl, biphenylyl or naphthyl are unsubstituted or substituted by 1–3 substituents selected from the group consisting of F, Cl, CF₃, methyl, methoxy and NR(7)R(8);
R(7) and R(8) are,
independently, H or alkyl having 1, 2, 3 or 4 carbon atoms;
or
R(1) is —OR(10) or —CR(10)R(11)R(12);
R(10) is —C$_f$H$_2$f-cycloalkyl having 3, 4, 5, 6, 7 or 8 carbon atoms in the cycloalkyl ring, or phenyl,
where phenyl is unsubstituted or substituted by 1–3 substituents selected from the group consisting of F, Cl, CF₃, CH₃, methoxy, hydroxyl, amino, methylamino and dimethylamino;
f is zero, 1 or 2;
R(11) and R(12) are,
independently of each other, defined as R(10) or are hydrogen or alkyl having 1, 2, 3 or 4 carbon atoms;

or

R(1) is phenyl, naphthyl, biphenylyl or heteroaryl having 1, 2, 3, 4, 5, 6, 7, 8 or 9 carbon atoms, with the latter being linked via a C atom or an N atom of the ring,
which are in each case unsubstituted or substituted by 1–3 substituents selected from the group consisting of F, Cl, CF₃, CH₃, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C|CR(18), —C[R(19)]=CHR(18), —C[R(20)R(21)]$_k$—(CO)—[CR(22)R(23)]$_l$—R(24),
k is zero, 1, 2, 3 or 4;
l is zero, 1, 2, 3 or 4;
R(13) and R(14) are,
identically or differently, —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);
R(17) is hydrogen or methyl,
g, h and i are,
identically or differently, zero, 1, 2, 3 or 4;
j is 1,2,3 or 4;
R(15) and R(16) are,
identically or differently, hydrogen, alkyl having 1, 2, 3, 4, 5 or 6 carbon atoms, or are, together with the carbon atom carrying them, cycloalkyl having 3, 4, 5, 6, 7 or 8 carbon atoms;
R(18) is
phenyl,
which is unsubstituted or substituted by 1–3 substituents selected from the group consisting of F, Cl, CF₃, methyl, methoxy and NR(25)R(26);
R(25) and R(26) are
H or alkyl having 1, 2, 3 or 4 carbon atoms;
or R
(18) is heteroaryl having 1, 2, 3, 4, 5, 6, 7, 8 or 9 carbon atoms which is unsubstituted or substituted as phenyl;
or
R(18) is alkyl having 1, 2, 3, 4, 5 or 6 carbon atoms which is unsubstituted or substituted by 1–3 OH;
or
R(18) is
cycloalkyl having 3, 4, 5, 6, 7 or 8 carbon atoms;
R(19), R(20), R(21), R(22) and R(23) are,
identically or differently, hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_2$m—R(18);
m is 1, 2, 3 or 4;
R(2) and R(3) are
defined as R(1);
R(4) is alkyl having 1, 2, 3 or 4 carbon atoms;
and the pharmaceutically tolerated salts thereof.

2. A compound of the formula I as claimed in claim 1, wherein
R(1) is H, F, Cl, Br, I, CN, NO₂, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;

X is oxygen;
a is zero or 1;
b is zero, 1 or 2;
c is zero, 1, 2 or 3;
or
R(1) is or —OR(10);
R(10) is —$C_fH_{2f}$-cycloalkyl having 3, 4, 5, 6, 7 or 8 carbon atoms in the cycloalkyl ring, or phenyl
where phenyl is unsubstituted or substituted by 1–3 substituents selected from the group consisting of F, Cl, $CF_3$, $CH_3$, methoxy, hydroxyl, amino, methylamino and dimethylamino;
f is zero or 1;
or
R(1) is phenyl, naphthyl, biphenylyl or heteroaryl having 1, 2, 3, 4, 5, 6, 7, 8 or 9 carbon atoms, with the latter being linked via a C atom or N atom of the ring,
which are unsubstituted or substituted by 1–3 substituents selected from the group consisting of F, Cl, $CF_3$, $CH_3$, methoxy, hydroxyl, amino, methylamino and dimethylamino,
or
R(1) is —SR(13), —OR(13), —NHR(13), —NR(13)R(14),—C≡CR(18) or —C[R(19)]=CHR(18);
R(13) and R(14) are,
identically or differently, —$(CH_2)_g$—$(CHOH)_h$—$(CH_2)_i$—$(CHOH)_j$—R(17) or —$(CH_2)_g$—O—$(CH_2$—$CH_2O)_h$—R(24);
R(17) is hydrogen or methyl,
g, h and i are,
identically or differently, zero, 1 or 2;
j is 1 or 2;
R(18) is
phenyl,
which is unsubstituted or substituted by 1–3 substituents selected from the group consisting of F, Cl, $CF_3$, methyl, methoxy and NR(25)R(26);
R(25) and R(26) are
H or alkyl having 1, 2, 3 or 4 carbon atoms;
or
R(18) is heteroaryl having 1, 2, 3, 4, 5, 6, 7, 8 or 9 carbon atoms, which is unsubstituted or substituted as phenyl;
or
R(18) is alkyl having 1, 2, 3, 4, 5 or 6 carbon atoms, which is unsubstituted or substituted by 1–3 OH;
or
R(18) is
cycloalkyl having 3, 4, 5, 6, 7 or 8 carbon atoms;
R(19) is hydrogen or methyl;
R(2) and R(3) are
defined as R(1);
R(4) is alkyl having 1 or 2 carbon atoms.

3. A compound of the formula I as claimed in claim 1 or 2, wherein
R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or $X_a$—$(CF_2)_c$—$CF_3$;
X is oxygen;
a is zero or 1;
c is zero or 1;
or
R(1) is or —OR(10);
R(10) is cycloalkyl having 4, 5 or 6 carbon atoms, or phenyl,
where phenyl is unsubstituted or substituted by 1–3 substituents selected from the group consisting of F, Cl, $CF_3$, $CH_3$, methoxy, hydroxyl, amino, methylamino and dimethylamino;
or
R(1) is quinolyl, isoquinolyl or pyridyl,
which are linked via a C atom or N atom of the ring;
and which are unsubstituted or substituted by 1–3 substituents selected from the group consisting of F, Cl, $CF_3$, $CH_3$, methoxy, hydroxyl, amino, methylamino and dimethylamino,
or
R(1) is phenyl,
which is unsubstituted or substituted by 1–3 substituents selected from the group consisting of F, Cl, $CF_3$, $CH_3$, methoxy, hydroxyl, amino, methylamino and dimethylamino,
or
R(1) is —C≡CR(18);
R(18) is
phenyl or cycloalkyl having five or 6 carbon atoms;
R(2) and R(3) are
defined as R(1);
R(4) is methyl.

4. A compound of the formula I as claimed in claim 1, wherein
R(1) is H, F, Cl, alkyl having 1, 2, 3 or 4 carbon atoms, alkoxy having 1, 2, 3 or 4 carbon atoms, cycloalkyl having 5 or 6 carbon atoms, cycloalkoxy having 5 or 6 carbon atoms or $X_a$—$CF_3$;
x is oxygen;
a is zero or 1;
R(2) and R(3) are
defined as R(1);
R(4) is methyl.

5. A process for preparing a compound I as claimed in claim 1, which comprises reacting a compound of the formula II

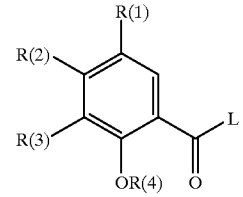

II in which R(1) to R(4) have the given meaning and L is a leaving group which can readily be substituted nucleophilically, with guanidine.

6. A compound according to claim 1 which is 2,3 dimethoxy-5-trifluoromethylbenzoylguanidine and the pharmaceutically tolerable salts thereof.

7. A compound according to claim 1 which is 2-methoxy-3-iodo-5-trifluoromethylbenzoylguanidine and the pharmaceutically tolerable salts thereof.

8. A compound according to claim 1 which is 2-methoxy-3-cyclopentyl-5-trifluoromethylbenzoylguandidine and the pharmaceutically tolerable salts thereof.

9. A compound according to claim 1 which is 2-methoxy-5-trifluoromethylbenzoylguanidine and the pharmaceutically tolerable salts thereof.

10. A compound according to claim 1 which is 2-methoxy-4-methylbenzoylguanidine and the pharmaceutically tolerable salts thereof.

11. A compound according to claim 1 which is 3,5-bis-tert-butyl-2-methoxybenzoylguanidine and the pharmaceutically tolerable salts thereof.

12. A compound according to claim 1 which is 2,4-dimethoxy-5-triflouromethylbenzoylguanidine and the pharmaceutically tolerable salts thereof.

13. The method of treating or preventing diseases brought about by ischemic conditions in a patient in need thereof comprising administering to the patient a therapeutically effective amount of a compound according to claim 1.

14. The method of treating or preventing cardiac infarction in a patient in need thereof comprising administering to the patient a therapeutically effective amount of a compound according to claim 1.

15. The method of treating or preventing angina pectoris in a patient in need therefo comprising administering to the patient a therapeutically effective amount of a compound according to claim 1.

16. The method of treating or preventing ischemic conditions of the heart in a patient in need thereof comprising administering to the patient a therapeutically effective amount of a compound according to claim 1.

17. The method of treating or preventing ischemic conditions of the peripheral and central nervous system and stroke in a patient in need thereof comprising administering to the patient a therapeutically effective amount of a compound according to claim 1.

18. The method of treating or preventing ischemic conditions of the peripheral organs and limbs in a patient in need thereof comprising administering to the patient a therapeutically effective amount of a compound according to claim 1.

19. The method of treating shock conditions in a patient in need thereof comprising administering to the patient a therapeutically effective amount of a compound according to claim 1.

20. The method of preparing a patient for a surgical operation or an organ transplantation comprising administering to the patient a therapeutically effective amount of a compound according to claim 1.

21. The method of preserving and storing a transplant organ for surgical transplantation comprising administering to the organ a therapeutically effective amount of a compound according to claim 1.

22. The method of treating diseases in which cell proliferation constitutes a primary or secondary cause including the treatment of atherosclerosis, complications of diabetes, cancer, fibrotic disease including pulmonary fibrosis, hepatic fibrosis or renal fibrosis, and prostate hyperplasia in a patient in need thereof comprising administering to the patient a therapeutically effective amount of a compound according to claim 1.

23. A pharmaceutical composition which comprises a therapeutically effective amount of a compound according to claim 1 in admixture with a physiologically acceptable carrier.

* * * * *

UNITED STATES PATENT AND TRADEMARK OFFICE
CERTIFICATE OF CORRECTION

PATENT NO. : 6,153,651  
DATED : November 28, 2000  
INVENTOR(S) : Udo Albus et al.

Page 1 of 1

It is certified that error appears in the above-identified patent and that said Letters Patent is hereby corrected as shown below:

<u>Column 12,</u>  
Line 12, "-C|CR(18)" should read -- C≡CR(18) --.  
Lines 40-41, "or R (18) is" should read -- or R(18) is --.

<u>Column 13,</u>  
Line 6, after "R(1) is", delete "or".  
Line 65, after "R(1) is", delete "or".

<u>Column 14,</u>  
Line 60, "trifluoromethylbenzoylguandidine" should read -- trifluoromethylbenzoylguanidine --.  
Line 66, "methylbenzoylguandidine" should read -- methylbenzoylguanidine --.

<u>Column 15,</u>  
Line 5, "triflouromethylbenzoylguanidine" should read -- trifluoromethylbenzoylguanidine --.  
Line 16, "therefo" should read -- thereof --.

Signed and Sealed this

Thirteenth Day of August, 2002

Attest:

JAMES E. ROGAN  
*Attesting Officer*  *Director of the United States Patent and Trademark Office*